United States Patent
Kinsho et al.

(10) Patent No.: US 9,126,920 B2
(45) Date of Patent: Sep. 8, 2015

(54) METHOD FOR PRODUCING 2-ISOPROPYLIDENE-5-METHYL-4-HEXENYL BUTYRATE

(71) Applicant: SHIN-ETSU CHEMICAL CO., LTD., Tokyo (JP)

(72) Inventors: Takeshi Kinsho, Niigata-ken (JP); Naoki Ishibashi, Niigata-ken (JP); Miyoshi Yamashita, Niigata-ken (JP); Yuki Miyake, Niigata-ken (JP); Akihiro Baba, Niigata-ken (JP); Yusuke Nagae, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/527,239

(22) Filed: Oct. 29, 2014

(65) Prior Publication Data
US 2015/0119597 A1 Apr. 30, 2015

(30) Foreign Application Priority Data
Oct. 30, 2013 (JP) ................................. 2013-225424

(51) Int. Cl.
*C07C 67/08* (2006.01)
*C07C 51/353* (2006.01)
*C07C 51/09* (2006.01)

(52) U.S. Cl.
CPC ............... *C07C 51/353* (2013.01); *C07C 51/09* (2013.01)

(58) Field of Classification Search
CPC .... C07C 29/132; C07C 67/14; C07C 67/333; A01N 31/02
See application file for complete search history.

(56) References Cited

PUBLICATIONS

Sugie et al, Applied Entomology and Zoology, Identification of a Sex Pheromone of the Japanese Mealy Bug *Planococcus kruniae* (Kuwana), 2008, pp. 369-375.*
Hinkins et al, Tetrahedron Letters, Identification and Synthesis of the Sex Pheromone of the Vine Mealybug, *Planococcus ficus*, 2001, 42, pp. 1619-1621.*
Matsui et al, Agricultural and Biological Chemistry, New Attempt at the Synthesis of Lavandulol by a Claisen Type Rearrangement, 1968, 32(10), pp. 1246-1249.*
The Total Synthesis of Natural Products, edited by ApSimon, John Wiley & Sons, vol. 7 (1988) 317-320.
Matsui, M. et al., *New Attempt at the Synthesis of Lavandulol by a Claisen Type Rearrangement*, Agric. Biol. Chem., vol. 32, No. 10 (1968) 1246-1249.
Sugie, H. et al., *Identification of a sex pheromone component of the Japanese mealybug, Planococcus kraunhiae (Kuwana)*, Appl. Entomol. Zool., 43(3) (2008) 369-375.
Tabata, J., *A convenient route for synthesis of 2-isopropyliden-5-methyl-4-hexen-1-yl butyrate, the sex pheromone of Planococcus kraunhiae (Hemiptera: Pseudococcidae), by use of B,γ to α,β double-bond migration in an unsaturated aldehyde*, Appl. Entomol. Zool., 48 (2013) 229-232.
European Search Report for Application No. 14 18 9828 dated Mar. 3, 2015.
Matsui, M. et al., *A New Synthetic Method of Lavandulols*, Agr. Biol. Chem., vol. 6, No. 10 (1962) 705-708.
Tabata, J., *A Convenient Route for Synthesis of 2-isopropylinden-5-methyl-4-hexen-1-yl Butyrate, the Sex Pheromone of Planococcus Kraunhiae (Hemiptera: Pseudococcidae), by Use of β,γ to α,β Double-Bond Migration in an Unsaturated Aldehyde*, Appl. Entomol. Zool., 48 (2013) 229-232.

* cited by examiner

Primary Examiner — Paul A Zucker
(74) Attorney, Agent, or Firm — Alston & Bird LLP

(57) ABSTRACT

Provided is a simple and efficient method for producing 2-isopropylidene-5-methyl-4-hexenyl butyrate. More specifically, provided is a method for producing 2-isopropylidene-5-methyl-4-hexenyl butyrate, the method including the steps of: isomerizing 2-isopropenyl-5-methyl-4-hexenoic acid ester (1) into 2-isopropylidene-5-methyl-4-hexenoic acid ester (2), reducing thus formed 2-isopropylidene-5-methyl-4-hexenoic acid ester (2) into 2-isopropylidene-5-methyl-4-hexenol (3), and butyrylating thus formed 2-isopropylidene-5-methyl-4-hexenol (3) into 2-isopropylidene-5-methyl-4-hexenyl butyrate (4),

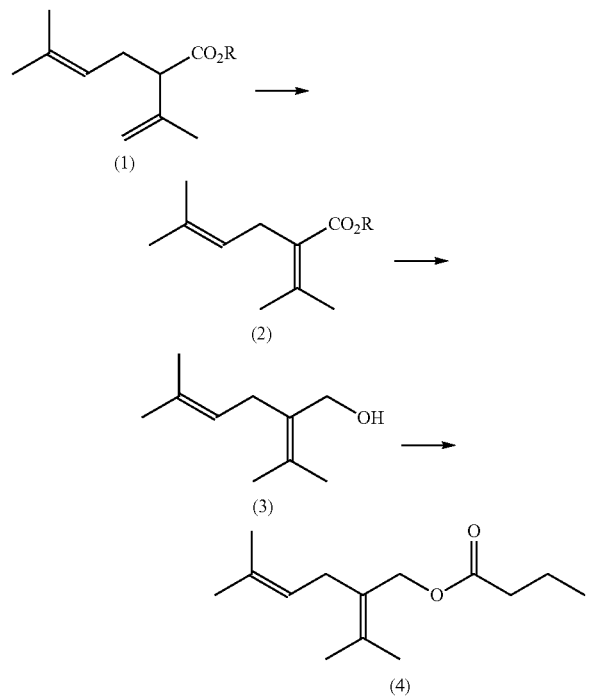

wherein R represents a $C_{1-10}$ hydrocarbon group.

9 Claims, No Drawings

METHOD FOR PRODUCING 2-ISOPROPYLIDENE-5-METHYL-4-HEXENYL BUTYRATE

FIELD

The present invention relates to a method for producing 2-isopropylidene-5-methyl-4-hexenyl butyrate (another name: fujikonyl butyrate), which is, for example, a sex pheromone of a Japanese mealybug, *Planococcus krauhinae* belonging to mealybug family.

BACKGROUND

Sex pheromones of insects are each a biologically active substance typically released from female individuals and having a function of attracting male individuals. They exhibit highly attractive activity even in small amounts. Sex pheromones have been used widely as means for forecasting the emergence or confirming geographical distribution (invasion into a specific area) of insect pests, or means for controlling insect pests. The means for controlling insect pests includes mass trapping, lure & kill or attract & kill, lure & infect or attract & infect, and mating disruption, which have been widely provided in practical use. Upon using sex pheromones, production of a necessary amount of each of the synthetic sex pheromones at a low cost is may be needed for basic research and moreover, for application.

A Japanese mealybug, *Planococcus kraunhiae* is an economically important insect pest distributed in Japan, China, Eritrea, and North America since it causes damage to many kinds of fruits. Sugie, et al., isolated the sex pheromone of this insect. The sex pheromone thus isolated coincided, in various spectra, with a compound (which is described as Compound A in the document) obtained in a yield of 0.2% under the acidic condition of the esterification reaction of 2-isopropenyl-5-methyl-4-hexenol (lavandulol) with butyryl chloride, and also various spectra coincided between their derivatives. As a result, the sex pheromone was determined to be 2-isopropylidene-5-methyl-4-hexenyl butyrate (fujikonyl butyrate) (App. Entomol. Zool., 43, 369-375(2008)).

Control of the Japanese mealybug using mating disruption is expected to be promising because of difficulty in conventional control using a pesticide. For fundamental biological research or agricultural research and moreover, for providing for application or practical use, a sufficient amount of synthetic pheromone should be supplied. There is therefore an eager demand for the development of a highly efficient and highly selective production method in which an amount of isomeric byproduct is small so that no purification is required.

Tabata has reported the synthesis of 2-isopropylidene-5-methyl-4-hexenyl butyrate in which 2-isopropenyl-5-methyl-4-hexenol as a starting material is subjected to an oxidation reaction with Dess-Martin reagent to form 2-isopropenyl-5-methyl-4-hexenal (lavandulal), the resulting aldehyde is isomerized under an acidic condition through migration of the double bond to form 2-isopropylidene-5-methyl-4-hexenal (another name: fujikonal), and the isomerized aldehyde is reduced and then esterified to form 2-isopropylidene-5-methyl-4-hexenyl butyrate (Appl. Entomol. Zool., 48, 229-232 (2013)).

SUMMARY

According to the description in Appl. Entomol. Zool., 48, 229-232 (2013), when 2-isopropylidene-5-methyl-4-hexenyl butyrate is synthesized as an intended product by using a method similar to that employed for the synthesis of Compound A described in Appl. Entomol. Zool., 43, 369-375 (2008), that is, through a reaction between lavandulol and butyryl chloride, the intended product can be obtained in a yield as low as from about 3 to 5% relative to an amount of 2-isopropenyl-5-methyl-4-hexenyl butyrate obtained through esterification of lavandulol without isomerization.

The method described in Appl. Entomol. Zool., 48, 229-232 (2013) is far from an industrial synthesis method because lavandulol to be used as a raw material is commercially available as a perfume, but a high cost limits availability of a large amount of it; the method employs Dess-Martin oxidation reaction requiring an expensive reagent and therefore being hard to apply industrially; silica gel column chromatography is used for isolation or purification of the intermediates; and the like.

Accordingly, in the conventional synthesis examples, it has been considered to be very difficult to industrially produce a sufficient amount of synthetic pheromone for practical use.

With the forgoing in view, the invention has been made. An object of the invention is to provide a simple and efficient method for producing 2-isopropylidene-5-methyl-4-hexenyl butyrate in order to supply a sufficient amount of synthetic pheromone of the Japanese mealybug for use in biological research, agricultural activity test, practical application or use, or the like.

With a view to achieving the above-mentioned object, the present inventors have proceeded with an extensive investigation. As a result, it has been found that 2-isopropylidene-5-methyl-4-hexenoic acid ester can be obtained by isomerizing 2-isopropenyl-5-methyl-4-hexenoic acid ester (lavandulic acid ester) under a basic condition; and the 2-isopropenyl-5-methyl-4-hexenoic acid ester or the carboxylic acid derived therefrom can be reduced and then butyrylated to industrially form 2-isopropylidene-5-methyl-4-hexenyl butyrate, which is the sex pheromone of the Japanese mealybug, leading to the completion of the invention.

In one aspect of the invention, there is provided a method for producing 2-isopropylidene-5-methyl-4-hexenyl butyrate, the method comprising the step of: isomerizing 2-isopropenyl-5-methyl-4-hexenoic acid ester represented by formula (1) into 2-isopropylidene-5-methyl-4-hexenoic acid ester represented by formula (2), reducing 2-isopropylidene-5-methyl-4-hexenoic acid ester (2) into 2-isopropylidene-5-methyl-4-hexenol represented by formula (3), and butyrylating 2-isopropylidene-5-methyl-4-hexenol (3) into 2-isopropylidene-5-methyl-4-hexenyl butyrate represented by formula (4),

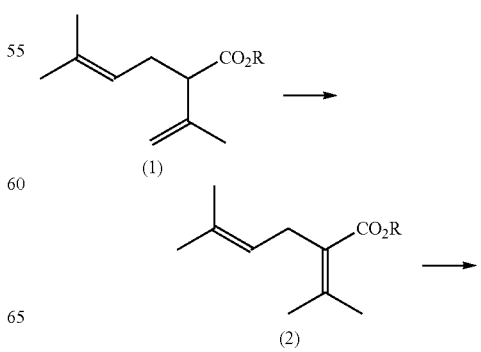

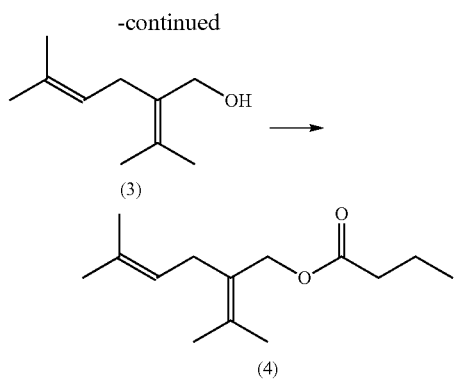

wherein R represents a hydrocarbon group having from 1 to 10 carbon atoms.

In one of the embodiments of the invention, there is also provided the method for producing 2-isopropylidene-5-methyl-4-hexenyl butyrate wherein the step of reducing comprises a stage of converting 2-isopropylidene-5-methyl-4-hexenoic acid ester (2) into 2-isopropylidene-5-methyl-4-hexenoic acid represented by formula (5), and a stage of reducing 2-isopropylidene-5-methyl-4-hexenoic acid (5) into 2-isopropylidene-5-methyl-4-hexenol (3).

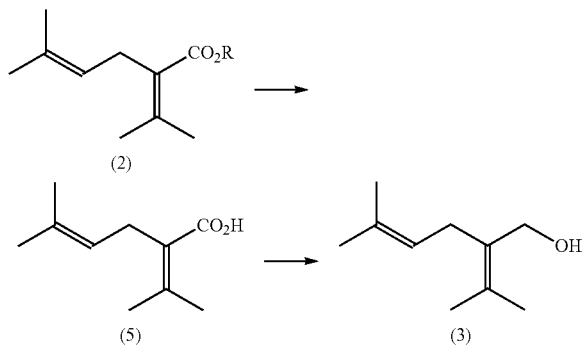

As described above, according to the invention, an industrial production method for efficiently synthesizing 2-isopropylidene-5-methyl-4-hexenyl butyrate is provided.

DETAILED DESCRIPTION

The embodiments of the invention will hereinafter be described specifically, but the invention is not limited to or by them.

According to the invention, the starting material is a 2-isopropenyl-5-methyl-4-hexenoic acid ester represented by the following formula (1):

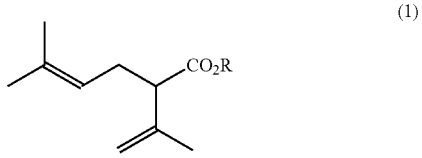

R represents a hydrocarbon group having from 1 to 10, preferably from 1 to 5 carbon atoms.

Examples of saturated hydrocarbon group contained by R include a linear, branched or cyclic saturated hydrocarbon group such as methyl, ethyl, n-propyl, n-butyl, n-pentyl, n-hexyl, n-heptyl, n-octyl, n-nonyl, n-decyl, cyclopropyl, cyclobutyl, cyclopentyl, cyclohexyl, cycloheptyl, cyclooctyl, bicyclo[2.2.1]heptyl, bicyclo[2.2.2]octyl, cyclopropylmethyl, cyclobutylmethyl, cyclopentylmethyl, cyclohexylmethyl, cycloheptylmethyl, cyclooctylmethyl, bicyclo[2.2.1]heptylmethyl, bicyclo[2.2.2]octylmethyl, cyclopropylethyl, cyclobutylethyl, cyclopentylethyl, cyclohexylethyl, cycloheptylethyl, cyclooctylethyl, bicyclo[2.2.1]heptylethyl, bicyclo[2.2.2]octylethyl, cyclopentylpropyl, cyclohexylpropyl, cycloheptylpropyl, cyclooctylpropyl, bicyclo[2.2.1]heptylpropyl, and bicyclo[2.2.2]octylpropyl.

Examples of unsaturated hydrocarbon group contained by R include a linear, branched or cyclic unsaturated hydrocarbon group such as vinyl, 1-propenyl, 2-propenyl, 2-methyl-1-propenyl, ethynyl, propynyl, 1-butynyl, cyclopentenyl, cyclohexenyl, dicyclohexadienyl, and methylcyclohexenyl. A hydrocarbon group which is an isomer of the above hydrocarbon group may also be included.

In addition, part or all of the hydrogen atoms contained by the saturated or unsaturated hydrocarbon group may be substituted with methyl, ethyl, n-propyl, isopropy, t-butyl, or the like.

An appropriate hydrocarbon group can be selected from these examples of the hydrocarbon group in consideration of reactivity in the later reaction or availability. For example, when an ester having R is selected as a substrate of a reduction reaction into 2-isopropylidene-5-methyl-4-hexenol (3) which will be described later, the R is preferably a lower alkyl group having a carbon atom number of 1 to 3 or a primary hydrocarbon group which causes less steric hindrance during the reduction reaction. When an ester having R is converted into the corresponding carboxylic acid of 2-isopropylidene-5-methyl-4-hexenoic acid through a hydrolysis reaction, a primary hydrocarbon group or a secondary hydrocarbon group facilitating the progress of the reaction is preferred. When it is converted into the corresponding carboxylic acid through an acid-catalyzed elimination reaction, a tertiary hydrocarbon group is preferred.

In view of them, particularly preferred examples of R include methyl, ethyl, n-propyl, n-butyl, cyclopentylmethyl, cyclohexylmethyl, isopropyl, isobutyl, sec-butyl, t-butyl, t-amyl, diethylmethylcarbinyl, triethylcarbinyl, cyclopentyldimethylcarbinyl, 1-methyl-1-cyclopentyl, 1-methyl-1-cyclohexyl, 1-ethyl-1-cyclopentyl, 1-ethyl-1-cyclohexyl, 1-isopropyl-1-cyclopentyl, 1-isopropyl-1-cyclohexyl, 1-t-butyl-1-cyclopentyl, 1-t-butyl-1-cyclohexyl, bicyclo[2.2.1]heptyl, 2-methyl-2-bicyclo[2.2.1]heptyl, 2-ethyl-2-bicyclo[2.2.1]heptyl, isobornyl, and 2-bicyclo[2.2.1]heptyldimethylcarbinyl.

The 2-isopropenyl-5-methyl-4-hexenoic acid ester (1) can be synthesized using a method such as the method described in "The Total Synthesis of Natural Products" edited by ApSimon, Vol. 7, 317-320, JOHN WILLEY & SONS, (1988) or the method in the references cited therein. Preferable examples of the method include the method of subjecting 2-methyl-3-buten-2-yl senecioate to Claisen type arrangement under a basic condition to obtain 2-isopropenyl-5-methyl-4-hexenoic acid and then esterifying 2-isopropenyl-5-methyl-4-hexenoic acid (Matsui et al., Agric., Biol. Chem., Vol. 32, 1246-1249(1968)) and the method of reacting the enolate of senecioic acid ester with a prenyl halide (1-halo-3-methyl-2-butene) for alkylation to obtain 2-isopropenyl-5-methyl-4-hexenoic acid ester.

Next, the step of isomerizing 2-isopropenyl-5-methyl-4-hexenoic acid ester (1) into the 2-isopropylidene-5-methyl-4-hexenoic acid ester (2) will be described.

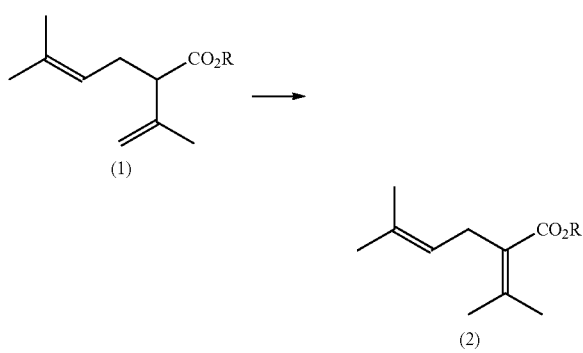

This isomerization reaction can be allowed to proceed under an acidic or basic condition. As a result of various investigations, it has been found that isomerization of an ester compound under a basic condition is particularly effective from the standpoint of selectivity, ease of reaction, and the like.

In the isomerization reaction under a basic condition, the reaction is typically carried out using a base in the presence of or in the absence of a solvent, with optional cooling or heating.

Examples of the base to be used for the isomerization reaction include alkoxides (preferably metal alkoxides, more preferably alkali metal alkoxides) such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; hydroxide salts (preferably metal hydroxides, more preferably alkali metal hydroxides or alkaline earth metal hydroxides) such as sodium hydroxide, lithium hydroxide, potassium hydroxide, and barium hydroxide; carbonates or bicarbonates (preferably alkali metal carbonates or alkali metal bicarbonates) such as sodium carbonate, potassium carbonate, sodium bicarbonate, and potassium bicarbonate; organometallic reagents such as methyllithium, ethyllithium, n-butyllithium, methylmagnesium chloride, and dimsylsodium; metal amides such as lithium diisopropylamide, lithium hexamethyldisilazide, sodium hexamethyldisilazide, and lithium dicyclohexylamide; metal hydrides such as sodium hydride, potassium hydride, and calcium hydride; and organic bases such as triethylamine, diisopropylethylamine, tributylamine, N,N-dimethylaniline, N,N-diethylaniline, pyridine, 4-dimethylaminopyridine, pyrrolidine, piperidine, collidine, lutidine, morpholine, and piperazine. The base may be used alone or as mixtures of any. The base can be selected in consideration of the type of substrate, reactivity, or selectivity.

Among the examples of the base, alkoxides are particularly preferred from the standpoint of selectivity and smooth progress of the intended reaction with a high yield. When the base is selected from the alkoxides, it is preferable to use a tertiary alkoxide having a low nucleophilicity so as to avoid more complex products as a result of ester exchange, or to use an alkoxide ROM corresponding to the R of the substrate, wherein M represents a cationic portion such as metal.

The amount of the base to be used for the isomerization reaction differs according to the type of substrate or base. It is, for example, from a catalytic amount (e.g. 0.5 mol or less, preferably from 0.001 to 0.5 mol) to a large excess (e.g. from 2 mol to 500 mol), preferably from 0.001 mol to a large excess, more preferably from 0.1 mol to a small excess (e.g. greater than 1 mol but not greater than 1.5 mol), each per mol of the ester compound as a substrate. When the reaction proceeds at a sufficiently fast rate, an amount of less than a stoichiometric amount is preferred from the economical viewpoint.

Examples of the solvent to be used for the isomerization reaction include water; alcohols such as methanol, ethanol, isopropyl alcohol, t-butyl alcohol, benzyl alcohol, methoxyethanol, ethoxyethanol, diethylene glycol monomethyl ether, and triethylene glycol monomethyl ether; ethers such as diethyl ether, di-n-butyl ether, tetrahydrofuran, and 1,4-dioxane; hydrocarbons such as hexane, heptane, benzene, toluene, xylene, and cumene; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); and nitriles such as acetonitrile and propionitrile. The solvent may be used alone or as mixtures of any. In the water-containing solvent, a carboxylic acid may be generated owing to hydrolysis, or another isomer may be generated owing to further migration of the double bond. Accordingly, the non-aqueous solvent is preferably selected. On the other hand, when it is intended to convert the ester as the substrate into the corresponding carboxylic acid in one pot, the water-containing solvent can be selected, or water can be added after isomerization. Regarding selection of the base and the solvent, when the above-mentioned alkoxide ROM is used, the alcohol (ROH) corresponding to the ROM can be preferably selected. The reaction using the alkoxide as the base in the water-containing solvent and the reaction using the hydroxide salt as the base in the alcohol solvent are considered to give the similar condition in the reaction system.

The reaction temperature in the isomerization reaction is preferably from −78° C. to the boiling point of the solvent, more preferably from −10° C. to 100° C. The reaction time can be desirably selected. It is preferable to allow the reaction to proceed sufficiently while monitoring the progress of the reaction with gas chromatography (GC) or thin-layer chromatography (TLC). The reaction time is typically and preferably from 5 minutes to 240 hours.

Although work-up of the reaction, that is, isolation or purification of an intended product can be carried out by using a method appropriately selected from typical purification methods in organic synthesis such as distillation under reduced pressure and various types of chromatography. The distillation under reduced pressure is preferred from the standpoint of industrial economy. When the crude intended product has a sufficiently high purity, it may be used without purification in the subsequent step.

The 2-isopropylidene-5-methyl-4-hexenoic acid ester (2) thus obtained can be directly subjected to a reduction reaction described later to form 2-isopropylidene-5-methyl-4-hexenol (3). Alternatively, it can be converted into 2-isopropylidene-5-methyl-4-hexenoic acid (5) and then subjected to be a reduction reaction. Particularly when 2-isopropylidene-5-methyl-4-hexenoic acid ester (2) is directly subjected to a reduction reaction described later, a side reaction such as 1,4-reduction which is thought to be likely to occur for sterically bulky R may occur. The side reaction can be avoided by converting it into 2-isopropylidene-5-methyl-4-hexenoic acid (5) once and then reducing it. By forming the acidic carboxylic acid as the intermediate before reduction, a neutral or basic impurity which may be generated in the side reaction may be removed by an aqueous work-up.

First, conversion of 2-isopropylidene-5-methyl-4-hexenoic acid ester (2) into 2-isopropylidene-5-methyl-4-hexenoic acid (5) will be described.

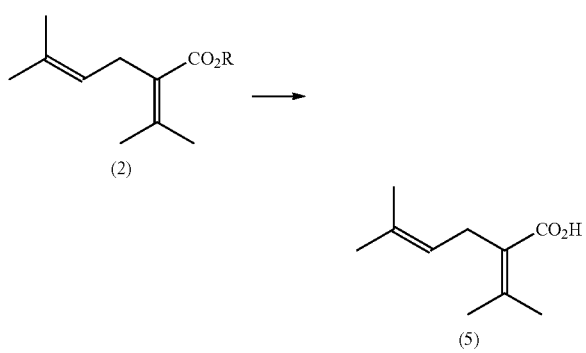

A conversion reaction from an ester to the corresponding carboxylic acid is applicable for the conversion of 2-isopropylidene-5-methyl-4-hexenoic acid ester (2) into 2-isopropylidene-5-methyl-4-hexenoic acid (5). Examples of the conversion reaction include a hydrolysis reaction under a basic or neutral condition, and an elimination reaction under an acidic condition.

The hydrolysis reaction is preferably used when R in the ester as the substrate is a primary or secondary hydrocarbon group. The elimination reaction under an acidic condition is preferably used when R is a tertiary hydrocarbon group. The hydrolysis reaction is carried out typically by using a base or a salt in a solvent, in the presence of water in the solvent or in later addition of water. The elimination reaction is carried out typically by using an acid in a solvent. In either reaction, the reaction may be carried out with optional cooling or heating.

Examples of the base to be used in the hydrolysis include hydroxide salts (preferably metal hydroxides, more preferably alkali metal hydroxides or alkaline earth metal hydroxides) such as sodium hydroxide, lithium hydroxide, potassium hydroxide, and barium hydroxide; carbonates or bicarbonates (preferably alkali metal carbonates or alkali metal bicarbonates) such as sodium carbonate, potassium carbonate, sodium bicarbonate, and potassium bicarbonate; and alkoxides (preferably metal alkoxides, more preferably alkali metal alkoxides) such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide.

Examples of the salts to be used in hydrolysis include halides (preferably alkali metal halides) such as lithium iodide, lithium bromide, trimethylsilyl iodide, and trimethylsilyl bromide.

Examples of the acid to be used in the elimination reaction include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide. The acid may be used alone or as mixtures of any.

Examples of the solvent to be used in the hydrolysis or elimination reaction include water; alcohols such as methanol, ethanol, isopropyl alcohol, t-butyl alcohol, benzyl alcohol, methoxyethanol, ethoxyethanol, diethylene glycol monomethyl ether, and triethylene glycol monomethyl ether; ethers such as diethyl ether, di-n-butyl ether, tetrahydrofuran, and 1,4-dioxane; hydrocarbons such as hexane, heptane, benzene, toluene, xylene, and cumene; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); and nitriles such as acetonitrile and propionitrile. The solvent may be used alone or as mixtures of any.

The reaction temperature and the reaction time in the conversion reaction into a carboxylic acid can be desirably selected. It is preferable to allow the reaction to proceed sufficiently, while monitoring the progress of the reaction with gas chromatography (GC) or thin-layer chromatography (TLC). The reaction temperature is preferably from −78° C. to the boiling point of the solvent, more preferably from −10° C. to 100° C. The reaction time is typically from 5 minutes to 240 hours.

Although work-up of the reaction, that is, isolation or purification of an intended product can be carried out by a method selected appropriately from typical purification methods in organic synthesis such as distillation under reduced pressure, recrystallization and various types of chromatography. The distillation under reduced pressure or recrystallization is preferred from the standpoint of industrial economy. Purification through recrystallization is of industrial value because the intended carboxylic acid may be isolated at a high purity from a mixture of isomers which are hard to be separated by distillation. When the crude intended product has a sufficiently high purity, it may be used without purification in the subsequent step.

Next, the 2-isopropylidene-5-methyl-4-hexenoic acid ester (2) or 2-isopropylidene-5-methyl-4-hexenoic acid (5) is subjected to a reduction reaction to form 2-isopropylidene-5-methyl-4-hexenol (3).

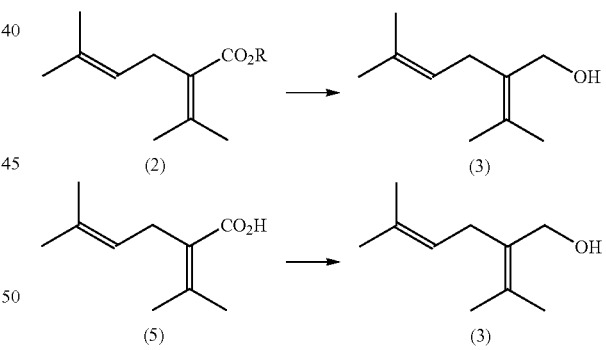

A reduction reaction from a carboxylic acid or ester into the corresponding alcohol is applicable for conversion of 2-isopropylidene-5-methyl-4-hexenoic acid (5) or its ester (2) thereof into 2-isopropylidene-5-methyl-4-hexenol (3). In the reduction reaction, a reducing agent is allowed to react with a reaction substrate usually in a solvent with optional cooling or heating. The reaction substrate may be selected depending on the type of the reducing agent or reaction condition. For example, when R in the ester is a primary or secondary alkyl group, the ester having R is preferably used as a substrate for reduction. When R is a tertiary alkyl group and its steric hindrance is particularly large, a side reaction such as 1,4-reduction may occur. Accordingly, in such a case, the ester having R is preferably converted into the corresponding carboxylic acid by the above-mentioned method, and then the resulting carboxylic acid is used as the substrate for reduction.

Examples of the reducing agent include hydrogen; boron compounds such as borane, alkylborane, dialkylborane, and bis(3-methyl-2-butyl)borane; metal hydrides such as dialkylsilane, trialkylsilane, alkylaluminum, dialkylaluminum, sodium hydride, lithium hydride, potassium hydride, and calcium hydride; complex hydrides such as sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri-tert-butoxyaluminum hydride, sodium bis(2-methoxyethoxy)aluminum hydride, lithium triethylborohydride, and diisobutylaluminum hydride; and alkoxy or alkyl derivatives thereof. The complex hydrides is preferred from the standpoint of reaction condition, ease of work-up, and ease of isolation of a product.

The amount of the reducing agent is selected according to the type of the reducing agent used or reaction condition, and the like. The amount thereof is preferably from 0.5 mol to a large excess (e.g. from 2 mol to 500 mol), more preferably form 0.9 to 8.0 mol per mol of the carboxylic acid or ester as the substrate.

Examples of the solvent to be used in the reduction reaction include water; hydrocarbons such as hexane, heptane, benzene, toluene, xylene, and cumene; ethers such as diethyl ether, dibutyl ether, diethylene glycol diethyl ether, diethylene glycol dimethyl ether, tetrahydrofuran, and 1,4-dioxane; alcohols such as methanol, ethanol, 1-propanol, 2-propanol, ethylene glycol monomethyl ether, and diethylene glycol monomethyl ether; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoric triamide. The solvent may be used alone or as mixtures of any.

The solvent to be used in the reduction reaction is selected according to the type of the reducing agent used. In a preferable combination of the reducing agent and the solvent, when lithium borohydride selected as the reducing agent, the solvent is selected from ethers, a mixed solvent of ether and alcohol, a mixed solvent of ether and hydrocarbon, and others. When lithium aluminum hydride is selected as the reducing agent, the solvent is selected from ethers, a mixed solvent of ether and hydrocarbon, and others.

The reaction temperature or the reaction time in the reduction reaction is selected in accordance with the type of the reagent or solvent used. For example, when lithium aluminum hydride in tetrahydrofuran is selected as the reducing agent, the reaction temperature is preferably from −78° C. to 50° C., more preferably from −70° C. to 20° C. The reaction time can be desirably selected. It is preferable from the standpoint of a yield to allow the reaction to be completed while monitoring the progress of the reaction with gas chromatography (GC) or thin-layer chromatography (TLC). The reaction time is typically from about 0.5 to 96 hours. Isolation or purification of the intended product, 2-isopropylidene-5-methyl-4-hexenol can be carried out using a method selected appropriately from typical purification methods in organic synthesis such as distillation under reduced pressure and various types of chromatography. The distillation under reduced pressure is preferable from the standpoint of industrial economy. When the crude intended product has a sufficient purity, it may be used without purification in the subsequent step.

According to the invention, the final step is of an esterification reaction in which 2-isopropylidene-5-methyl-4-hexenol (3) is butyrylated into the intended target product, 2-isopropylidene-5-methyl-4-hexenyl butyrate (4).

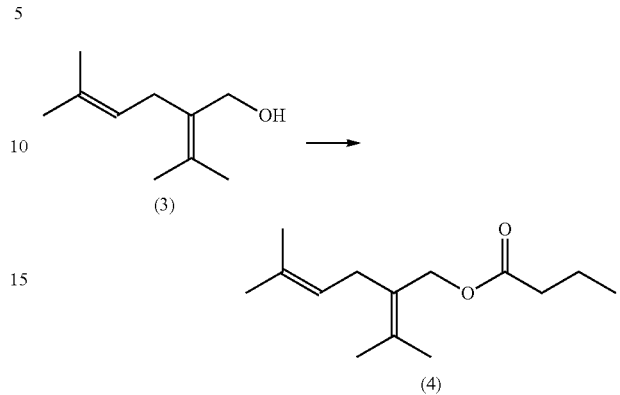

As this esterification reaction, a reaction for producing an ester is applicable including a reaction of an alcohol with an acylating agent, a reaction of an alcohol with a carboxylic acid, an ester exchange reaction, and a combination of a reaction for converting an alcohol into the corresponding alkylating agent and a reaction of the alkylating agent with a carboxylic acid.

Regarding the reaction of the alcohol with the acylating agent, examples of the solvent include chlorine-based solvents such as methylene chloride, chloroform, and trichloroethylene; hydrocarbons such as hexane, heptane, benzene, toluene, xylene, and cumene; ethers such as diethyl ether, dibutyl ether, diethylene glycol diethyl ether, diethylene glycol dimethyl ether, tetrahydrofuran, and 1,4-dioxane; nitriles such as acetonitrile; ketones such as acetone and 2-butanone; esters such as ethyl acetate and n-butyl acetate, and aprotic polar solvents such as N,N-dimethylformamide, dimethylsulfoxide, and hexamethylphosphoric triamide. The solvent may be used alone or as mixtures of any.

To the above-mentioned solvent, 2-isopropylidene-5-methyl-4-hexanol (3) which is the reaction substrate, the acylating agent and base are added successively or simultaneously for the reaction. The acylating agent includes butyryl chloride, butyryl bromide, butyric anhydride, mixed acid anhydrides such as: butyric trifluoroacetic anhydride, butyric methanesulfonic anhydride, butyric trifluoromethanesulfonic anhydride, butyric benzenesulfonic anhydride, butyric acid and p-toluenesulfonic anhydride, and p-nitrophenyl butyrate. The base includes triethylamine, diisopropylethylamine, N,N-dimethylaniline, pyridine, and 4-dimethylaminopyridine.

The reaction using the acylating agent such as acid anhydride can also be carried out, instead of using the base, in the presence of an acid catalyst selected from inorganic acids such as hydrochloric acid, hydrobromic acid, sulfuric acid, and nitric acid; and organic acids such as oxalic acid, trifluoroacetic acid, methanesulfonic acid, benzenesulfonic acid, and p-toluenesulfonic acid.

The reaction temperature for the reaction of the alcohol with the acylating agent can be selected appropriately according to the type of the acylating agent used or reaction condition. The reaction temperature is preferably from −50° C. to the boiling point of the solvent, more preferably from −20° C. to room temperature (from 5° C. to 35° C.). The amount of the acylating agent is preferably from 1 to 40 mol, more preferably from 1 to 5 mol, each per mol of the alcohol compound as the reactant.

Regarding the reaction of the alcohol with the carboxylic acid, the reaction of 2-isopropylidene-5-methyl-4-hexenol (3) with butyric acid is a dehydration reaction and is commonly carried out in the presence of an acid catalyst. The amount of butyric acid is preferably from 1 to 40 mol, more preferably from 1 to 5 mol, each per mol of 2-isopropylidene-5-methyl-4-hexenol.

Examples of the acid catalyst to be used in the reaction of the alcohol with the carboxylic acid include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide. The acid may be used alone or as mixtures of any.

The amount of the acid catalyst in the reaction of the alcohol with the carboxylic acid is preferably from 0.001 to 1 mol, more preferably from 0.01 to 0.05 mol, each per mol of the 2-isopropylidene-5-methyl-4-hexenol.

The solvent to be used in the reaction of the alcohol with the carboxylic acid includes the same examples as those of the solvent for the reaction with the acylating agent. The reaction temperature may be selected appropriately according to the type of the acylating agent or reaction condition. The reaction temperature is typically preferably from −50° C. to the boiling point of the solvent, more preferably from room temperature (from 5° C. to 35° C.) to the boiling point of the solvent. The reaction may be allowed to proceed while azeotropically removing water formed out of the system by using a solvent containing a hydrocarbon such as hexane, heptane, benzene, toluene, xylene, or cumene. In the azeotropic distillation, water may be distilled off while refluxing at the boiling point of the solvent under normal pressure, or water may be distilled off at a temperature lower than the boiling point thereof under reduced pressure.

Regarding the ester exchange reaction, the alkyl butyrate is reacted with 2-isopropylidene-5-methyl-4-hexenol (3) in the presence of a catalyst, while the resulting alcohol is removed. The alkyl butyrate in the ester exchange reaction is preferably a primary alkyl ester of butyric acid, particularly preferably methyl butyrate, ethyl butyrate, and n-propyl butyrate from the standpoint of cost and smooth progress of the reaction. The amount of the alkyl butyrate is preferably from 1 to 40 mol, more preferably from 1 to 5 mol, each per mol of 2-isopropylidene-5-methyl-4-hexenol.

Examples of the catalyst to be used in the ester exchange reaction include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; bases such as sodium methoxide, sodium ethoxide, potassium t-butoxide, and 4-dimethylaminopyridine; salts such as sodium cyanide, potassium cyanide, sodium acetate, potassium acetate, calcium acetate, tin acetate, aluminum acetate, aluminum acetoacetate, and alumina; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide. The acid may be used singly or as a mixture of two or more acids.

The amount of the catalyst in the ester exchange reaction is preferably from 0.001 to 20 mol, more preferably from 0.01 to 0.05 mol, each per mol of 2-isopropylidene-5-methyl-4-hexenol. The reaction can be carried out in a solvent-free manner or the alkyl butyrate itself serving as a reaction reagent may be used as a solvent. The reaction in the absence of solvent is preferable in standpoint of the absence of an extra operation such as concentration or solvent recovery. The solvent can also be used in an auxiliary manner.

Examples of the solvent to be used in the ester exchange reaction include hydrocarbons such as hexane, heptane, benzene, toluene, xylene, and cumene; and ethers such as diethyl ether, dibutyl ether, diethylene glycol diethyl ether, diethylene glycol dimethyl ether, tetrahydrofuran, and 1,4-dioxane. The solvent may be used alone or as mixtures of any.

The reaction temperature for the ester exchange reaction may be selected appropriately according to the type of the alkyl butyrate used or reaction condition. The reaction is typically carried out with heating. Good results can be obtained by carrying out the reaction at a temperature around the boiling point of a low-boiling-point lower alcohol such as methanol, ethanol, or 1-propanol generated as a result of the ester exchange reaction, while removing the lower alcohol thus generated. The alcohol may be distilled off under reduced pressure at a temperature lower than the boiling point.

Regarding a combination of the reaction for converting the alcohol into the corresponding alkylating agent and the reaction of the alkylating agent with the carboxylic acid, for example, 2-isopropylidene-5-methyl-4-hexenol (3) is converted into the corresponding halide (chloride, bromide, or iodide) or the corresponding sulfonic acid ester such as methanesulfonic acid ester, trifluoromethanesulfonic acid ester, benzenesulfonic acid ester, or p-toluenesulfonic acid ester, and then the halide or sulfonic acid ester is reacted with butyric acid typically in a solvent under a basic condition.

The solvent, base, reaction time, and reaction temperature to be used in the combination of the reaction for converting the alcohol into the corresponding alkylating agent and the reaction of the alkylating agent with the carboxylic acid may be the same as those described in the reaction of the alcohol with the acylating agent. Instead of a combination of butyric acid and the base, a butyrate salt such as sodium butyrate, lithium butyrate, potassium butyrate, or ammonium butyrate may be used.

The isolation or purification of the intended product, 2-isopropylidene-5-methyl-4-hexenyl butyrate can be carried out using a method selected appropriately from typical purification methods used in organic synthesis such as distillation under reduced pressure and various types of chromatography. The distillation under reduced pressure is preferable from the standpoint of industrial economy.

As described above, a simple and efficient method for producing 2-isopropylidene-5-methyl-4-hexenyl butyrate, which is the pheromone of a Japanese mealybug can be carried out so that a sufficient amount of synthetic pheromone necessary for application or use can be provided.

EXAMPLES

The invention will hereinafter be described more specifically by Examples. However, it should not be construed that the invention is limited to or by them.

The term "purity" as used hereinafter is a value determined by gas chromatography (GC) analysis unless otherwise specifically indicated.

Synthesis Example 1

Synthesis 1 of 2-isopropenyl-5-methyl-4-hexenoic Acid (1) as a Starting Material Having Formula (1) Wherein R is a Hydrogen Atom In a nitrogen atmosphere, a mixture of the 40.3 mmol of sodium hydride, obtained from 1.61 g of 60% suspension in mineral oil by removal of mineral oil with n-hexane washing, and 50 ml of toluene was heated to reflux while being stirred. Then, 6.76 g of 2-methyl-3-buten-2-yl senecioate having a purity of 96.2% was added dropwise thereto over one hour. After reflux was continued for 80 minutes, 50 ml of diethyl ether was added thereto and 2 ml of methanol was added dropwise thereto. Then, 60 ml of water was added thereto to separate an aqueous phase. The aqueous phase thus separated was made acidic in addition of 20% hydrochloric acid, followed by extracted with diethyl ether. The diethyl ether solution was subjected to typical work-up including washing, drying and concentration to obtain 7.69 g of the crude intended product. The crude yield was 89%.

GC analysis revealed that the crude product was a 45.7:54.2 mixture of 2-isopropylidene-5-methyl-4-hexenoic acid ($\alpha,\beta$-unsaturated carboxylic acid) and 2-isopropenyl-5-methyl-4-hexenoic acid ($\beta,\gamma$-unsaturated carboxylic acid) and had a purity of 78.0% in total.

Synthesis Example 2

Synthesis 2 of 2-isopropenyl-5-methyl-4-hexenoic Acid as a Starting Material Having Formula (1) Wherein R is a Hydrogen Atom In a nitrogen atmosphere, a mixture of 117 g of hexamethyldisilazane and 600 ml of tetrahydrofuran was cooled with ice. The mixture was subjected to dropwise addition of 425 ml of a 1.65M solution of n-butyllithium in n-hexane over one hour, followed by stirring for 30 minutes. Then, the resulting mixture was cooled to $-60°$ C. while being stirred. A mixture of 118 g of 2-methyl-3-buten-2-yl senecioate having a purity of 97.8% and 100 g of tetrahydrofuran was added dropwise thereto over 75 minutes. After gradually heating to room temperature, the mixture was stirred for 6 hours and then cooled again with ice. To the mixture cooled with ice was added 286 g of a 10% aqueous solution of sodium hydroxide to separate the aqueous phase. After addition of 400 g of 20% hydrochloric acid to the aqueous phase thus separated, the resulting mixture was extracted with diethyl ether. The diethyl ether solution was subjected to typical work-up including washing, drying and concentration to obtain 109.1 g of the crude intended product having a purity of 94.6%. The yield was 90%.

GC analysis revealed that the crude product contained no 2-isopropylidene-5-methyl-4-hexenoic acid ($\alpha,\beta$-unsaturated carboxylic acid) and had a sufficient purity as a starting material so that it was used without purification in the subsequent step.

Synthesis Example 3

Synthesis of ethyl 2-isopropenyl-5-methyl-4-hexenoate Having Formula (1) Wherein R is $C_2H_5$ In a nitrogen atmosphere, a mixture of 200.01 g of 2-isopropenyl-5-methyl-4-hexenoic acid having a purity of 85.4%, 89.82 g of potassium carbonate, 11.28 g of tetrabutylammonium chloride, and 800 g of toluene was heated to from 95° C. to 100° C., while being stirred. Then, 191.8 g of diethyl sulfate was added dropwise thereto over 35 minutes. After heating was continued for 2 hours, the reaction mixture was cooled to room temperature and 510 g of water was added thereto. The toluene solution was separated and then subjected to typical work-up including washing, drying and concentration to obtain the crude product.

The crude product was distilled under reduced pressure to obtain 193.4 g of the intended product having a purity of 99.7%. The yield was 97%.

Synthesis Example 4

Synthesis of t-butyl 2-isopropenyl-5-methyl-4-hexenoate Having Formula (1) Wherein R is $C(CH_3)_3$ In a nitrogen atmosphere, a mixture of 190 g of hexamethyldisilazane and 700 ml of tetrahydrofuran was cooled to $-20°$ C. To the mixture was added dropwise 670 ml of a 1.64 M solution of n-butyllithium in n-hexane over 25 minutes, followed by stirring for 40 minutes. Then, the mixture was cooled to from $-40°$ C. to $-50°$ C. while being stirred. A mixture of 162 g of t-butyl senecioate having a purity of 96.6% and 100 ml of tetrahydrofuran was added dropwise thereto over 22 minutes, and then stirred at $-50°$ C. or lower for 40 minutes. A mixture of 142.5 g of 1-bromo-3-methyl-2-butene and 100 ml of tetrahydrofuran was added dropwise thereto over 35 minutes. The resulting mixture was gradually heated to 2° C. over 2 hours, followed by stirring at 30° C. for 40 minutes. The reaction mixture was poured into an aqueous ammonium chloride solution cooled with ice, followed by extraction with n-hexane. The n-hexane solution was subjected to typical work-up including washing, drying and concentration to obtain 249.2 g of the crude product. The yield was 91%.

GC analysis revealed that the resulting crude product was a 97.4:2.6 mixture of t-butyl 2-isopropenyl-5-methyl-4-hexenoate ($\beta,\gamma$-unsaturated ester) and t-butyl 2-isopropylidene-5-methyl-4-hexenoate ($\alpha,\beta$-unsaturated ester) and had a purity of 81.9% in total. The crude product had a sufficient purity as a starting material so that it was used without purification in the subsequent step.

Example 1

Synthesis of ethyl 2-isopropylidene-5-methyl-4-hexenoate Having Formula (2) Wherein R is $C_2H_5$ Isomerization of $\beta,\gamma$-Unsaturated Ester to $\alpha,\beta$-Unsaturated Ester In a nitrogen atmosphere, 35.0 g of potassium t-butoxide was added at room temperature to a mixture of 303 g of ethyl 2-isopropenyl-5-methyl-4-hexenoate having a purity of 75.3% and an isomeric ratio of $\beta,\gamma$-unsaturated ester to $\alpha,\beta$-unsaturated ester of 96.7:3.3 and corresponding to formula (1) wherein R is $C_2H_5$, and 2000 ml of tetrahydrofuran, and stirred for 15.5 hours at room temperature. The resulting reaction mixture was poured into ice water, followed by extraction with n-hexane. The n-hexane solution was subjected to typical work-up including washing, drying and concentration to obtain 258.61 g of the crude product having a purity of 77.6% and an isomeric ratio of β,γ-unsaturated ester to α,β-unsaturated ester of 8.8:91.2.

The crude product was purified by distillation under reduced pressure to obtain 110.8 g of intended product having a purity of 93.1%, and an isomeric ratio of β,γ-unsaturated ester to α,β-unsaturated ester of 0:100. The yield was 49%. The fractions inferior in purity or isomeric ratio were provided for the isomerization reaction again for recycling. A total yield calculated as a sum of weight multiplied by purity with respect to all the fractions including the fractions for recycling was 84%.

Ethyl 2-isopropylidene-5-methyl-4-hexenoate Having Formula (2) Wherein R is $C_2H_5$ IR (D-ATR): ν=2980, 2916, 1711, 1635, 1446, 1375, 1279, 1211, 1170, 1072 $cm^{-1}$.

$^1$H-NMR (500 MHz, $CDCl_3$): δ=1.28 (3H, t, J=7.1 Hz), 1.65-1.67 (6H, m), 1.80 (3H, s), 1.96 (3H, s), 2.99 (2H, d, J=6.9 Hz), 4.17 (2H, q, J=7.1 Hz), 5.01-5.06 (1H, m) ppm.

$^{13}$C-NMR (125 MHz, $CDCl_3$): δ=14.27, 17.73, 21.74, 22.89, 25.66, 28.90, 59.98, 121.64, 127.19, 132.00, 141.54, 169.66 ppm Example 2

Synthesis of ethyl 2-isopropylidene-5-methyl-4-hexenoate Having Formula (2) Wherein R is $C_2H_5$ Re-Isomerization of Mixture of β,γ-Unsaturated Ester and α,β-Unsaturated Ester A 21.4 g mixture of ethyl 2-isopropenyl-5-methyl-4-hexenoate and ethyl 2-isopropylidene-5-methyl-4-hexenoate, corresponding to formulae (1) and (2) where R is $C_2H_5$, respectively, had a purity of 92.7% in total and an isomeric ratio of β,γ-unsaturated ester to α,β-unsaturated ester of 23.8:76.2. This 21.4 g mixture and a mixture of 0.5 g of potassium t-butoxide and 10 ml of toluene were stirred at room temperature for 1.5 hours. After the reaction mixture was treated in the same manner as in Example 1, the mixture had a isomeric ratio of β,γ-unsaturated ester to α,β-unsaturated ester of 8.9:91.1, indicating the possibility of re-isomerization.

Example 3

Synthesis of ethyl 2-isopropylidene-5-methyl-4-hexenoate Having Formula (2) Wherein R is $C_2H_5$ Isomerization of β,γ-Unsaturated Ester into α,β-Unsaturated Ester A mixture of 0.50 g of ethyl 2-isopropenyl-5-methyl-4-hexenoate having a purity of 75.5% and an isomeric ratio of β,γ-unsaturated ester to α,β-unsaturated ester of 96.7:3.3 and corresponding to formula (1) wherein R is $C_2H_5$, 0.70 g of 20% solution of sodium ethoxide in ethanol, and 5 ml of tetrahydrofuran was refluxed for 7.5 hours while being stirred. After the reaction mixture was treated in the same manner as in Example 1, the mixture had the isomeric ratio of β,γ-unsaturated ester to α,β-unsaturated ester of 13.7:86.3. The spectra of the mixture coincided with those of Example 1.

Example 4

Synthesis of t-butyl 2-isopropylidene-5-methyl-4-hexenoate Having Formula (2) Wherein R is $C(CH_3)_3$ Isomerization of β,γ-Unsaturated Ester into α,β-Unsaturated Ester and Purification of the Latter In a nitrogen atmosphere, 25.0 g of potassium t-butoxide was added at room temperature to a mixture of 256.8 g of t-butyl 2-isopropenyl-5-methyl-4-hexenoate having a purity of 81.9% and an isomeric ratio of β,γ-unsaturated ester to α,β-unsaturated ester of 97.4:2.6 and corresponding formula (1) wherein R is $C(CH_3)_3$, and 1000 ml of t-butyl alcohol, and stirred overnight at room temperature. The reaction mixture was poured into ice water, followed by extraction with n-hexane. The n-hexane solution was subjected to typical work-up including washing, drying and concentration to obtain 228.65 g of the crude product having a purity of 81.5% and an isomeric ratio of β,γ-unsaturated ester to α,β-unsaturated ester of 10.2:89.8.

The crude product was purified by distillation under reduced pressure to obtain, as the intended product, 34.34 g of a fraction having a purity of 94.2% and an isomeric ratio of β,γ-unsaturated ester to α,β-unsaturated ester of 1.7:98.3, and 54.28 g of a fraction having a purity of 90.4% and an isomeric ratio of β,γ-unsaturated ester to α,β-unsaturated ester of 0.2:99.8. A total yield of the two fractions was 38%. The fractions inferior in purity or isomeric ratio were provided for recycling. A total yield calculated as a sum of weight multiplied by purity of all the fractions including the fraction for recycling was 80%.

t-Butyl 2-isopropylidene-5-methyl-4-hexenoate Having Formula (2) Wherein R is $C(CH_3)_3$ IR (D-ATR): ν=2977, 2928, 2859, 1711, 1367, 1158, 1073 $cm^{-1}$.

$^1$H-NMR (500 MHz, $CDCl_3$): δ=1.47 (9H, s), 1.65-1.67 (6H, m), 1.76 (3H, s), 1.90 (3H, s), 2.94 (2H, d, J=6.8 Hz), 5.04-5.07 (1H, m) ppm.

Example 5

Synthesis of t-butyl 2-isopropylidene-5-methyl-4-hexenoate Having Formula (2) Wherein R is $C(CH_3)_3$ Re-Isomerization of a Mixture of β,γ-Unsaturated Ester and α,β-Unsaturated Ester In a nitrogen atmosphere, 10.0 g of potassium t-butoxide was added to a mixture of 112.55 g of t-butyl 2-isopropenyl-5-methyl-4-hexenoate having a purity of 92.3% and an isomeric ratio of β,γ-unsaturated ester to α,β-unsaturated ester of 16.7:83.2 and corresponding to formula (1) wherein R is $C(CH_3)_3$, 300 ml of t-butyl alcohol and 100 ml of tetrahydrofuran at room temperature, and stirred overnight at room temperature. After the reaction mixture was treated in the same manner as in Example 4, 117.34 g of the crude product having a purity of 87.9% and an isomeric ratio of β,γ-unsaturated ester to α,β-unsaturated ester of 10.1:89.9 was obtained.

Comparative Example 1

When 2-isopropenyl-5-methyl-4-hexenoic acid (β,γ-unsaturated carboxylic acid) was synthesized in Synthesis Example 1, 2-isopropylidene-5-methyl-4-hexenoic acid (α,β-unsaturated carboxylic acid) was produced as a by-product and a ratio of the by-product increased particularly in the later stage of the reaction. Accordingly, a test was performed to verify whether the method is practical for a synthesis route of α,β-unsaturated carboxylic acid or not.

After the substrate and the reagent were reacted with each other in the same manner as in Synthesis Example 1, reflux was continued for long hours, while monitoring the reaction by GC analysis of the reaction mixture. The isomeric ratio of α,β-unsaturated carboxylic acid to β,γ-unsaturated carboxylic acid was 68.8:31.2 at cumulative reflux time of 70 minutes, 38.1:61.9 at cumulative reflux time of 110 minutes, and 31.6:68.4 at cumulative reflux time of 555 minutes. In GC analysis, two kinds of peaks of isomers, which were presumed not to correspond to those of the intended product, appeared in a retention time region overlapping with that of the β,γ-unsaturated carboxylic acid. Generation of complex isomer mixture was found, revealing that direct isomerization of carboxylic acid under the above-mentioned basic condition is not practical as a method for producing an α,β-unsaturated carboxylic acid.

Comparative Example 2

In a nitrogen atmosphere, a catalytic amount (20 mg) of p-toluenesulfonic acid monohydrate was added to a mixture of 0.55 g of 2-isopropenyl-5-methyl-4-hexenoic acid and 10 ml of o-xylene and heated to reflux. As a result of GC-MS analysis of the reaction mixture, it was found that the intended α,β-unsaturated carboxylic acid was in a trace amount and a main product was intramolecularly cyclized 2-isopropylidene-5-hydroxy-5-methylhexanoic acid γ-lactone. It has been revealed that direct isomerization of carboxylic acid under the above-mentioned acidic condition is not practical as a method for producing an α,β-unsaturated carboxylic acid.

Example 6

Synthesis of 2-isopropylidene-5-methyl-4-hexenoic acid (5)

Conversion from Ester

In a nitrogen atmosphere, 160 ml of 22.5% perchloric acid was added to a mixture of 97.0 g of t-butyl 2-isopropylidene-5-methyl-4-hexenoate having a purity of 87.9% and an α,β-isomer purity of 89.9% and corresponding to formula (2) wherein R is C(CH$_3$)$_3$ and 2000 ml of tetrahydrofuran, and stirred for 25 hours at from 60° C. to 80° C. The reaction mixture was poured into ice water, followed by extraction with n-hexane. The n-hexane extract was extracted twice with 100 ml of a 10% aqueous sodium hydroxide solution for separation into an organic phase and an aqueous phase. The organic phase was subjected to work-up including drying and concentration to recover 61.76 g of the starting material t-butyl ester having a purity of 75.1%, an α,β-isomer purity of 87.6% in the recovery yield of 54%.

On the other hand, the aqueous layer (aqueous sodium hydroxide solution extract) was subjected to addition of 100 ml of 20% hydrochloric acid, and extracted with a 1:1 (volume ratio) mixture of tetrahydrofuran and toluene. The resulting organic phase was subjected to work-up including washing, drying and concentration to obtain 29.57 g of the crude product having a purity of 94.6% and an α,β-isomer purity of 93.0%. The yield was 44%.

The crude product was recrystallized from n-hexane to obtain 15.69 g of intended product having a purity of 98.0% and an α,β-isomer purity of 89.9%.

2-Isopropylidene-5-methyl-4-hexenoic acid (5)

IR (D-ATR): ν=2996, 2966, 2923, 1683, 1611, 1292, 1236, 932 cm$^{-1}$.

$^1$H-NMR (500 MHz, CDCl$_3$): δ=1.67-1.69 (6H, m), 1.87 (3H, s), 2.10 (3H, s), 3.03 (2H, d, J=6.9 Hz), 5.03-5.07 (1H, m), 11.90-12.70 (1H, br. s) ppm.

$^{13}$C-NMR (125 MHz, CDCl$_3$): δ=17.79, 23.00, 23.49, 25.68, 28.75, 121.80, 126.02, 132.07, 147.80, 175.03 ppm

Example 7

Synthesis 1 of 2-isopropylidene-5-methyl-4-hexenol (3)

Reduction of Ester Corresponding to Formula (2) Wherein R is C$_2$H$_5$

In a nitrogen atmosphere, a mixture of 10.6 g of ethyl 2-isopropylidene-5-methyl-4-hexenoate having a purity of 97.3% and an α,β-isomer purity of 95.7% and corresponding to formula (2) wherein R is C$_2$H$_5$ and 40 ml of tetrahydrofuran was added dropwise to a mixture of 2.23 g of lithium aluminum hydride and 80 ml of tetrahydrofuran over 10 minutes which was stirred under cooling with ice. The reaction mixture was stirred under cooling with ice for one hour and at room temperature for two hours, and then 4 ml of ethyl acetate, 2.23 ml of water, 2.23 ml of 15% sodium hydroxide, and 6.69 ml of water were added carefully thereto in this order while stirring, and crystals thus formed were filtered out. The filtrate was dried and concentrated to obtain 8.48 g of the crude product having a purity of 85.9% and an α,β-isomer purity of 95.2%. The yield was 90%.

The crude product thus obtained had a sufficient purity as an intermediate so that it was used without purification in the subsequent step.

2-Isopropylidene-5-methyl-4-hexenol (3)

IR (D-ATR): ν=3332, 2966, 2915, 2878, 2857, 1445, 1375, 1000 cm$^{-1}$.

$^1$H-NMR (500 MHz, CDCl$_3$): δ=1.42-1.43 (1H, br. s), 1.68-1.69 (6H, m), 1.71 (3H, s), 1.75 (3H, s), 2.85 (2H, d, J=7.3 Hz), 4.09 (2H, s), 5.05-5.09 (1H, m) ppm.

$^{13}$C-NMR (125 MHz, CDCl$_3$): δ=17.73, 20.14, 20.48, 25.72, 29.69, 62.23, 122.64, 130.02, 131.33, 132.06 ppm

Example 8

Synthesis 2 of 2-isopropylidene-5-methyl-4-hexenol (3)

Reduction of Ester Having Formula (2) Wherein R is C(CH$_3$)$_3$

A mixture of 34.3 g of t-butyl 2-isopropylidene-5-methyl-4-hexenoate (2) having a purity of 94.2% and an α,β-isomer purity of 98.3% and corresponding to formula (2) wherein R is C(CH$_3$)$_3$, and 50 ml of tetrahydrofuran was added dropwise to a mixture of 5.50 g of lithium aluminum hydride and 100 ml of tetrahydrofuran over 15 minutes which was stirred under cooling with ice. The reaction mixture was heated and stirred at 50° C. for one hour, and then cooled with ice again. While stirring, 20 ml of ethyl acetate, 5.5 ml of water, 5.5 ml of 15% sodium hydroxide and 16.5 ml of water were added carefully thereto in this order, and crystals thus formed were filtered out. The filtrate was dried and concentrated to obtain 24.45 g of the crude product having a purity of 48.1% and an α,β-isomer purity of 96.2%. The yield was 50%.

The crude product contained, as main byproducts, 2-isopropyl-5-methyl-4-hexenal (49.4% GC) and 2-isopropyl-5-methyl-4-hexenol (3) (2.4% GC).

Example 9

Synthesis of 2-isopropylidene-5-methyl-4-hexenol (3)

Reduction of Carboxylic Acid (5)

A mixture of 5.0 g of 2-isopropylidene-5-methyl-4-hexenoic acid (5) having a purity of 98.0% and an α,β-isomer purity of 98.3% and 50 ml of tetrahydrofuran was added dropwise to a mixture of 2.25 g of lithium aluminum hydride and 40 ml of tetrahydrofuran over 40 minutes which was stirred under cooling with ice. The reaction mixture was heated and stirred at room temperature for two days, and then cooled with ice again. While stirring, 5 ml of ethyl acetate, 2.25 ml of water, 2.25 ml of 15% sodium hydroxide and 6.75 ml of water were added carefully thereto in this order, and crystals thus formed were filtered out. The filtrate was dried and concentrated to obtain 4.66 g of the crude product having a purity of 90.8% and an α,β-isomer purity of 97.7%. The yield was 94%.

The spectra of the crude product coincided with those of Example 7. The crude product had a sufficient purity as an intermediate so that it was used without purification in the subsequent step.

Example 10

Synthesis of 2-isopropylidene-5-methyl-4-hexenyl butyrate (4)

In a nitrogen atmosphere, 64.0 g of butyryl chloride was added dropwise to a mixture of 94.1 g of 2-isopropylidene-5-methyl-4-hexenol (3) having a purity of 81.1% and an α,β-isomer purity of 98.1%, 50 g of pyridine and 500 ml of acetonitrile over 55 minutes which was stirred under cooling with ice. The reaction mixture was stirred for 2 hours under cooling with ice. To the reaction mixture was added an aqueous solution of saturated sodium bicarbonate, followed by extraction with diethyl ether. The diethyl ether solution was subjected to work-up including washing, drying and concentration to obtain 131.22 g of the crude product. The crude product was purified by distillation under reduced pressure to obtain, as the intended product, 23.54 g of a fraction having a purity of 92.8% and an α,β-isomer purity of 97.0% and 82.05 g of a fraction having a purity of 92.2% and an α,β-isomer purity of 98.3%. The yield of fractions including the other fractions was 95%.

2-Isopropylidene-5-methyl-4-hexenyl butyrate (4)

IR (D-ATR): ν=2966, 2931, 2876, 1734, 1451, 1375, 1174, 1098, 966 cm$^{-1}$.

$^{1}$H-NMR (500 MHz, CDCl$_{3}$): δ=0.94 (3H, t, J=7.4 Hz), 1.58-1.70 (8H, m), 1.73 (3H, s), 1.75 (3H, s), 2.28 (2H, t, J=7.5 Hz), 2.79 (2H, d, J=7.2 Hz), 4.56 (2H, s), 4.98-5.02 (1H, m) ppm.

$^{13}$C-NMR (125 MHz, CDCl$_{3}$): δ=13.66, 17.66, 18.49, 20.42, 20.61, 25.70, 29.61, 36.27, 63.66, 122.08, 126.81, 131.93, 132.58, 173.91 ppm

The invention claimed is:

1. A method for producing 2-isopropylidene-5-methyl-4-hexenyl butyrate, comprising the steps of:
   isomerizing 2-isopropenyl-5-methyl-4-hexenoic acid ester represented by formula (1):

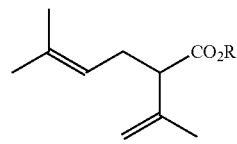

(1)

in the presence of metal alkoxide into 2-isopropylidene-5-methyl-4-hexenoic acid ester represented by formula (2):

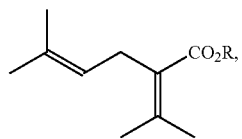

(2)

reducing the 2-isopropylidene-5-methyl-4-hexenoic acid ester (2) into 2-isopropylidene-5-methyl-4-hexenol represented by formula (3):

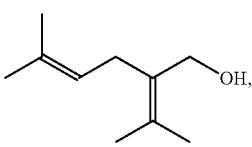

(3)

and
butyrylating the 2-isopropylidene-5-methyl-4-hexenol (3) into 2-isopropylidene-5-methyl-4-hexenyl butyrate represented by formula (4):

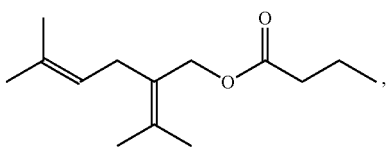

(4)

wherein R represents a hydrocarbon group having from 1 to 10 carbon atoms.

2. The method for producing 2-isopropylidene-5-methyl-4-hexenyl butyrate according to claim 1, wherein the step of reducing comprises:
   converting the 2-isopropylidene-5-methyl-4-hexenoic acid ester (2) into 2-isopropylidene-5-methyl-4-hexenoic acid represented by formula (5):

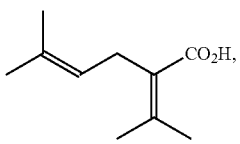
(5)

and reducing the 2-isopropylidene-5-methyl-4-hexenoic acid (5) into 2-isopropylidene-5-methyl-4-hexenol (3).

3. The method for producing 2-isopropylidene-5-methyl-4-hexenyl butyrate according to claim 1, wherein R is selected from the group consisting of methyl, ethyl, n-propyl, n-butyl, cyclopentylmethyl, cyclohexylmethyl, isopropyl, isobutyl, sec-butyl, t-butyl, t-amyl, diethylmethylcarbinyl, triethylcarbinyl, cyclopentyldimethylcarbinyl, 1-methyl-1-cyclopentyl, 1-methyl-1-cyclohexyl, 1-ethyl-1-cyclopentyl, 1-ethyl-1-cyclohexyl, 1-isopropyl-1-cyclopentyl, 1-isopropyl-1-cyclohexyl, 1-t-butyl-1-cyclopentyl, 1-t-butyl-1-cyclohexyl, bicyclo[2.2.1]heptyl, 2-methyl-2-bicyclo[2.2.1]heptyl, 2-ethyl-2-bicyclo[2.2.1]heptyl, isobornyl, and 2-bicyclo[2.2.1]heptyldimethylcarbinyl.

4. The method for producing 2-isopropylidene-5-methyl-4-hexenyl butyrate according to claim 1, wherein the metal alkoxide comprises one or more of sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide.

5. The method for producing 2-isopropylidene-5-methyl-4-hexenyl butyrate according to claim 4, wherein the metal alkoxide is a tertiary alkoxide.

6. The method for producing 2-isopropylidene-5-methyl-4-hexenyl butyrate according to claim 1, wherein isomerization takes place in the presence of a solvent.

7. The method for producing 2-isopropylidene-5-methyl-4-hexenyl butyrate according to claim 6, wherein the solvent comprises one or more of water, alcohols, ethers, hydrocarbons, aprotic polar solvents, and nitriles.

8. The method for producing 2-isopropylidene-5-methyl-4-hexenyl butyrate according to claim 1, wherein isomerization takes place at a temperature from −10° C. to 100° C.

9. The method for producing 2-isopropylidene-5-methyl-4-hexenyl butyrate according to claim 2, wherein 2-isopropylidene-5-methyl-4-hexenoic acid (5) is reduced to 2-isopropylidene-5-methyl-4-hexenol (3) by a reducing agent selected from the group consisting of hydrogen, boron compounds, metal hydrides, and complex hydrides.

* * * * *